(12) United States Patent
Stemmer (10) Patent No.: US 10,031,201 B2
(45) Date of Patent: Jul. 24, 2018

(54) METHOD AND APPARATUS FOR MAGNETIC RESONANCE IMAGING

(71) Applicant: Siemens Aktiengesellschaft, Munich (DE)

(72) Inventor: Alto Stemmer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 301 days.

(21) Appl. No.: 15/074,298

(22) Filed: Mar. 18, 2016

(65) Prior Publication Data
US 2016/0274205 A1    Sep. 22, 2016

(30) Foreign Application Priority Data
Mar. 19, 2015    (DE) .......................... 10 2015 204 955

(51) Int. Cl.
*G01R 33/54*    (2006.01)
*G01R 33/3875*    (2006.01)
(Continued)

(52) U.S. Cl.
CPC ....... *G01R 33/543* (2013.01); *G01R 33/3875* (2013.01); *A61B 5/055* (2013.01); *G01R 33/243* (2013.01); *G01R 33/56563* (2013.01)

(58) Field of Classification Search
CPC ........ G01R 33/00; G01R 33/20; G01R 33/08; G01R 33/38; G01R 33/3875; G01R 33/44;
(Continued)

(56) References Cited

U.S. PATENT DOCUMENTS

| 7,554,327 B2 * | 6/2009 | Dewdney ........... G01R 33/3875 324/319 |
| 8,199,992 B2 * | 6/2012 | Ritter ............... G01R 33/56518 382/131 |

(Continued)

OTHER PUBLICATIONS

Blamire et al: "Dynamic Shim Updating: A new approach towards optimized whole brain shimming", MRM, vol. 36, pp. 159-165, (1996).
(Continued)

*Primary Examiner* — Hoai-An D Nguyen
(74) *Attorney, Agent, or Firm* — Schiff Hardin LLP (57) ABSTRACT

To enable improved reconstruction of magnetic resonance (MR) image data from MR scan data acquired from an examination object using dynamic shimming in an MR scanner that has a shim unit with at least one shim channel, an examination region of the object is divided into multiple sections, a B0 field of the examination region is scanned, and a B0 field map is thereby generated, a number of shim parameter sets are determined for the shim channel using the B0 field map, with a first shim parameter set of the number of shim parameter sets being determined for a first section of the multiple sections, and a second shim parameter set of the multiple shim parameter sets is determined for a second section of the multiple sections. MR scan data of the examination region are acquired, but before acquiring the MR scan data from the first section, the shim channel is adjusted using the first shim parameter set and, before acquiring the MR scan data from the second section, the shim channel is adjusted using the second shim parameter set. MR image data are reconstructed from the MR scan data using the first B0 field map and the number of shim parameter sets.

12 Claims, 2 Drawing Sheets

(51) Int. Cl.
*G01R 33/24* (2006.01)
*G01R 33/565* (2006.01)
*A61B 5/055* (2006.01)

(58) Field of Classification Search
CPC ...... G01R 33/46; G01R 33/54; G01R 33/543; G01R 33/5659; G01R 33/243; G01R 33/56563; A61B 5/055
USPC .......................................... 324/300, 307, 309
See application file for complete search history.

(56) References Cited

U.S. PATENT DOCUMENTS

| | | | | |
|---|---|---|---|---|
| 9,841,476 | B2* | 12/2017 | Stemmer | A61B 5/055 |
| 2005/0154291 | A1 | 7/2005 | Zhao et al. | |
| 2007/0279060 | A1 | 12/2007 | Dannels et al. | |
| 2008/0088306 | A1* | 4/2008 | Dewdney | A61B 5/055 |
| | | | | 324/309 |
| 2009/0302845 | A1* | 12/2009 | Biber | G01R 33/3415 |
| | | | | 324/318 |
| 2012/0163692 | A1* | 6/2012 | Harvey | G01R 33/5659 |
| | | | | 382/131 |
| 2012/0249137 | A1 | 10/2012 | Witschey et al. | |
| 2015/0293198 | A1* | 10/2015 | Grodzki | A61B 5/055 |
| | | | | 324/309 |
| 2016/0154076 | A1* | 6/2016 | Dewdney | G01R 33/3873 |
| | | | | 324/307 |
| 2016/0209484 | A1* | 7/2016 | Bauer | G01R 33/543 |

OTHER PUBLICATIONS

Morell et al.: "Dynamic Shimming for Multi-Slice Magnetic Resonance Imaging", MRM, vol. 38, pp. 477-483, (1997).
Jezzard et al. Correction for Geometric Distortion in Echo Planar Images from B0 Field Variations, MRM vol. 38, pp. 55-73 (1995).
Hutton et al., "Image Distortion Correction in fMRI: A Quantitative Evaluation," NeuroImage, vol. 16, pp. 217-240 (2002).
Munger et al., "An Inverse Problem Approach to the Correction of Distortion in EPI Images," IEEE Transactions on Medical Imaging, vol. 19, No. 7, pp. 681-689 (2000).
Kadah et al., "Algebraic Reconstruction for Magnetic Resonance Imaging Under $B_0$ Inhomogeneity," IEE Transactions on Medical Imaging, vol. 17, No. 3, pp. 362-370 (1998).

* cited by examiner

METHOD AND APPARATUS FOR MAGNETIC RESONANCE IMAGING

BACKGROUND OF THE INVENTION

Field of the Invention

The invention relates to a method for magnetic resonance imaging, a magnetic resonance apparatus and a data storage medium encoded with programming instructions to implement such a method.

Description of the Prior Art

In the scanner of a magnetic resonance apparatus, also called a magnetic resonance tomography system, the body of an examination person, in particular a patient, to be examined is conventionally exposed with by a basic field magnet to a relatively high basic magnetic field, for example of 1.5 or 3 or 7 tesla. In addition, gradient pulses are produced by the operation of a gradient coil arrangement. Radio-frequency pulses, for example excitation pulses, are then emitted by a radio-frequency antenna arrangement by suitable antenna devices, and this leads to the nuclear spins of specific atoms excited in a resonant manner by these radio-frequency pulses being tilted by a defined flip angle with respect to the magnetic field lines of the basic magnetic field. As the nuclear spins relax, radio-frequency signals, known as magnetic resonance signals, are radiated that are received by suitable radio-frequency antennas and then processed further. Finally, the desired image data can be reconstructed from the raw data acquired in this way.

For a specific scan, a specific magnetic resonance sequence, also called a pulse sequence, is emitted that includes a sequence of radio-frequency pulses, for example excitation pulses and refocusing pulses, and appropriate gradient pulses that are to be emitted in a coordinated manner in various gradient axes in various directions. At a time appropriate therewith, readout windows are set, which specify the periods in which the induced magnetic resonance signals are detected.

The homogeneity of a basic magnetic field in an examination volume is very important in magnetic resonance imaging by such a magnetic resonance apparatus. Even small deviations in the homogeneity can lead to large deviations in the frequency distribution of the nuclear spins, so poor quality magnetic resonance image data are recorded. For example, magnetic resonance recording methods, such as echo planar imaging, place high demands on the homogeneity of the basic magnetic field.

The examination object itself constitutes a source of inhomogeneity. If, for example, a person to be examined is introduced into the magnetic resonance device, the material of the body interferes with the homogeneity of the basic magnetic field.

To counter this problem it is known to use an adjustable shim unit. By operation of this shim unit, a shim process, known as "in vivo shimming", can be carried out individually for different examination objects. In this shim process, first a local B0 field in an examination region is conventionally scanned, wherein a B0 field map, also called a B0 field map or B0 map, is created. Constant shim currents (DC offset currents), which flow through gradient coils of the magnetic resonance device, are ascertained using the B0 field map. Furthermore, using the B0 field map currents can be calculated for specific shim channels of a higher order, which can compensate the local field distortions. After adjustment of these currents a resonance frequency is usually ascertained in a frequency adjustment for desired spectral components of an examined tissue, in particular of protons bound to water. The DC offset shim currents through the gradient coils and/or the currents for the shim channels of a higher order and/or the resonance frequency can then form a shim parameter set, which is used for acquiring magnetic resonance image data.

It is known that compensation of local field distortions functions all the more completely the smaller a volume is in which the main magnetic field is to be homogenized. It can therefore make sense to ascertain various shim parameter sets for a plurality of sections of the examination region separately and to adjust the shim unit differently using the various shim parameter sets for acquiring magnetic resonance image data from the plurality of sections. Rapid switching-over of the shim currents and resonance frequency during a runtime of the magnetic resonance sequence for acquiring the magnetic resonance image data on a sequence-dependent timescale of a few milliseconds to a few seconds may be necessary. For this reason, this type of shim process is also conventionally called dynamic shimming. Conventional shimming with a single set of parameters for the whole examination region will be called global shimming below.

Dynamic shimming is described, for example, in the document Blamire et al., "Dynamic Shim Updating: A New Approach Towards Optimized Whole Brain Shimming", 1996, MRM, 36, 159-165 and in the document Morrell et al., "Dynamic shimming for Multi-Slice Magnetic Resonance Imaging", 1997, MRM, 38, 477-483.

The accuracy with which local inhomogeneities of the basic magnetic field are compensated depends on the number and order of existing and usable shim channels. In modern MR systems, linear shim terms are usually generated, for example in the three directions, by the DC offset currents through the three gradient coils. Due to the linear field characteristic in the gradient directions, the gradient coils filled with the static shim currents can then be called shim channels of the first order. Furthermore, magnetic resonance devices have dedicated shim coils. These dedicated shim coils can then form shim channels of a higher order, for example of the second order. Shim channels of this kind are often constructed such that the compensation fields which they generate can be described by spherical harmonics. Since the order of the corresponding spherical harmonics is limited, however, it is not usually possible to completely correct fields that vary quickly in the vicinity of susceptibility interfaces. These shim channels can therefore generate compensation fields of a higher order. For example, typical shim channels of the second order comprise five shim coils.

The gradient coils and associated gradient amplifiers are typically designed such that the gradient fields can be varied on a timescale of a few microseconds, for example of roughly ten microseconds. This is usually sufficient for dynamic shimming. By contrast, the field of shim channels of a higher order is typically adjusted only after a settle time of the order of a second or a few seconds. This is frequently not enough for dynamic shimming. The cause of this can be due to the design since faster adjustment of these shim channels demands more powerful amplifiers and/or possibly wires having low resistance. This can increase the costs of the magnetic resonance apparatus. The space that is available to the shim coils of the shim channels of a higher order can potentially also be limited, or the installation of appropriately modified shim channels of a higher order can require a new design or a disadvantageous design of other components of the system.

For these reasons often only the shim channels of the first order, namely conventionally the gradient coils, and/or an RF center frequency, are dynamically switched in a dynamic shim process. Therefore typically only the currents in the shim channels of the first order vary during the runtime of the magnetic resonance sequence. In the shim channels of a higher order a current is conventionally adjusted once before the scan. This current should then be kept constant across the scan. The constant current can correspond to a device-specific tune-up value or, as described above, be ascertained in a specific "in vivo" adjustment carried out in advance for the examination object.

SUMMARY OF THE INVENTION

An object of the invention is to improve the reconstruction of magnetic resonance image data from magnetic resonance scan data that are acquired using dynamic shimming.

The inventive method for magnetic resonance imaging an examination object in an examination region by operation of a scanner of magnetic resonance apparatus, having a shim unit having at least one shim channel, includes the following steps. The examination region is divided into multiple sections. The basic magnetic field (B0 field) produced by the scanner in the examination region is scanned, with a first B0 field map then being generated. Multiple shim parameter sets are ascertained for the at least one shim channel using the first B0 field map, with a first shim parameter set of the multiple shim parameter sets being ascertained for a first section of the multiple sections, and a second shim parameter set of the multiple shim parameter sets is ascertained for a second section of the multiple sections. Magnetic resonance scan data of the examination region of the examination object are acquired, wherein, before acquiring the magnetic resonance scan data from the first section, the at least one shim channel is set using the first shim parameter set and, before acquiring the magnetic resonance scan data from the second section, the at least one shim channel is set using the second shim parameter set. Magnetic resonance image data are reconstructed from the magnetic resonance scan data using the first B0 field map and the multiple shim parameter sets.

The examination region, also called field of view (FOV), is a volume that is mapped in the magnetic resonance image data reconstructed from the magnetic resonance scan data. The examination region is typically defined by a user, for example on a topogram (localizes). Of course the examination region can alternatively or additionally also be defined automatically, for example on the basis of a chosen protocol. The examination object can be a patient, training person, an animal or a phantom. The reconstructed magnetic resonance image data is, in particular, supplied, i.e. displayed for a user on a display unit and/or stored in a database.

According to the inventive approach, the examination region has multiple sections, namely at least one first section and one second section. The examination region can of course also have further sections that are different from the first and second sections. A single excitation slice of the magnetic resonance sequence can be a section of the examination region. The number of sections of the examination region can therefore be equal to the number of excitation slices of the examination region. Of course larger sections of the examination region containing, for example, a number of adjacent slices, or smaller sections, are also conceivable. The magnetic resonance scan data are acquired individually from the respective sections of the examination region for each of the multiple sections. After the acquisition of magnetic resonance data from a first section, magnetic resonance data are typically acquired from other sections before renewed acquisition of magnetic resonance data from the first section occurs. There are applications, however, in which firstly all data are acquired from a first section before data are acquired from a second section.

The at least one shim channel can have one shim channel or multiple shim channels. A shim channel can be formed by a gradient coil of the magnetic resonance device. It is also conceivable for a shim channel to be formed by a dedicated shim coil of the shim unit. The at least one shim channel can generate shim fields of the first order, in particular linear shim fields. Theoretically it is also conceivable for a shim channel to generate shim fields of a higher order, for example of the second order.

As described, during acquisition of the magnetic resonance scan data the at least one shim channel can be supplied with different shim currents. The shim currents in the at least one shim channel therefore can be switched-over for acquisition of magnetic resonance scan data from different sections of the examination region. For example, the at least one shim channel can be filled with different shim currents for acquisition of magnetic resonance scan data from different slices of the examination region. In this way a field contribution can be varied for a homogenization of the main magnetic field due to the shim currents flowing through the at least one shim channel during acquisition of the magnetic resonance scan data. The at least one shim channel is therefore advantageously designed for dynamic shimming.

The method includes scanning the B0 field in order to generate a B0 field map, such as by a method familiar to those skilled in the art. A B0 field map is a field distribution of the basic magnetic field of the magnetic resonance scanner. The B0 field map at least approximately reproduces the deviation of the physical B0 field from an ideal constant main magnetic field of the magnetic resonance device. The B0 field map thus can be used to identify inhomogeneities in the main magnetic field that occur, for example, when the examination object is positioned in the magnetic resonance device. The B0 field map produced by the scanning will be called the first B0 field map below.

One shim parameter set of the multiple shim parameter sets can include adjustments for controlling a shim unit of the magnetic resonance apparatus, in particular of the at least one shim channel of the shim unit. For example, the shim parameter set can define a current of the at least one shim channel. A shim control unit, in particular an adjusting unit, can then load the at least one shim channel during recording of the magnetic resonance scan data with the currents defined by the shim parameter set. The shim parameter set can have a suitable value for the RF center frequency and/or resonance frequency. The RF center frequency will hereinafter formally be treated like a shim channel (shim channel of the $0^{th}$ order). The multiple shim parameter sets are designed so as to be different from each other. They have, for example, different current values for the at least one shim channel and/or different frequency values for the RF center frequency.

A first shim parameter set for a first section of the examination region can then be ascertained using the first B0 field map such that the inhomogeneities of the basic magnetic field are at least partly compensated by the shim parameter set used on the at least one shim channel during acquisition of the magnetic resonance scan data from the first section. A second shim parameter set for a second section of the examination region can accordingly be ascertained using the first B0 field map such that the inhomogeneities of the main magnetic field are at least partly compensated by the second shim parameter set used on the at least one shim channel during acquisition of the magnetic resonance scan data from the second section. In this way the first B0 field map constitutes an advantageous starting point for ascertaining the plurality of shim parameter sets.

Magnetic resonance scan data can be acquired, for example, by radiation of RF pulses and applying slice selection gradients, phase coding gradients and frequency coding gradients and recording the resulting magnetic resonance signals by a radio-frequency coil. The magnetic resonance scan data are typically only the raw data that the acquired magnetic resonance signals contain after demodulation. The magnetic resonance scan data are therefore not typically directly available to an expert for diagnosis. Instead, magnetic resonance image data, which typically constitute at least one magnetic resonance image data record, is reconstructed using the magnetic resonance scan data. The magnetic resonance image data can then be made available, displayed on a display unit, to an expert, e.g. a radiologist, to create a diagnosis.

According to the inventive approach dynamic shimming by means of the at least one shim channel should be carried out during acquisition of the magnetic resonance scan data. The at least one shim channel is therefore adjusted for acquisition of magnetic resonance scan data from various sections of the examination region using various shim parameter sets of the plurality of shim parameter sets. In this way the basic magnetic field of the magnetic resonance scanner in the specific section can be homogenized using the associated specific shim parameter set for acquisition of the magnetic resonance scan data from a specific section of the examination region.

The use of dynamic shimming can reduce and/or prevent signal loss during acquisition of the magnetic resonance scan data. Such signal losses can occur if, for example, a local field gradient at the location of a pixel is so large that a phase characteristic within the pixel is of the order of $2\pi$ or more, so the signal dephases strongly. Furthermore, signal losses occur if specific B0 sensitive methods, such as the gradient reversal method, are used for fat suppression. Dynamic shimming advantageously prevents or reduces signal losses which would be irreversible during subsequent reconstruction of the magnetic resonance image data. Generally, dynamic shimming is more suitable than global shimming having only one center frequency and one shim parameter set for the whole examination region.

According to the inventive approach, the multiple shim parameter sets and the first B0 field map are then incorporated in the reconstruction of the magnetic resonance image data from the magnetic resonance scan data. The multiple shim parameter sets and the first B0 field map thus can constitute input parameters for an algorithm which is used for reconstruction of the magnetic resonance image data. Various possibilities are described in the following as to how the multiple shim parameter sets and the first B0 field map can be incorporated in the reconstruction of the magnetic resonance image data. A preferred method is a "field mapping technique" using a second B0 field map, which is calculated using the first B0 field map and the plurality of shim parameter sets. This approach is described in more detail below. Of course the multiple shim parameter sets can also be incorporated in the reconstruction of the magnetic resonance image data by a different method that is considered appropriate to those skilled in the art.

Particularly when using an echo planar imaging method (EPI) for acquiring the raw data, local B0 deviations lead to distortions in the phase coding direction in the images reconstructed from the raw data. The use of the multiple shim parameter sets in the reconstruction of the magnetic resonance image data can be particularly advantageous since the specific adjustment of the shim currents and/or center frequency for the various sections of the examination region. The slice-specific adjustment can lead to adjoining pixels of various slices being able to exhibit different distortions. This can make diagnosis of the magnetic resonance image data, in particular diagnosis of an image data characteristic, for example a lesion, difficult in a direction perpendicular to an imaging plane of a single slice.

A decisive reason for this is that typically only shim channels with a lower order, for example up to the first order, can be used for the dynamic shimming. The corresponding linear field characteristic of the compensation fields cannot correct all B0 inhomogeneities and not all distortions therefore. While, as a rule, this is more successful in dynamic shimming than in global shimming of the whole examination region with a single parameter set, since the basic magnetic field only has to be homogenized in a smaller section of the examination region in each case, as a rule, not all shim channels can be used in dynamic shimming, in particular owing to the frequently long settling times of the shim channels of the second order or higher.

It should be noted that the change to the center frequency corresponds to a shift of all pixels in the slice by a constant value. A gradient generates a pixel shift that increases linearly with the distance from the isocenter in the gradient direction. The B0 inhomogeneities that actually occur, and therewith distortions, are significantly more complex. In the case of dynamic shimming adjacent pixels, which are allocated to the various sections, are also distorted differently due to the various shim adjustments. This leads to an unnatural course of the anatomy in the corresponding direction.

The multiple shim parameter sets can be incorporated in the reconstruction of the magnetic resonance image data such that distortions of this kind are avoided and/or reduced in the magnetic resonance image data. A signal loss in the acquired magnetic resonance scan data or in the reconstructed magnetic resonance image data can simultaneously be avoided and a distortion of the magnetic resonance image data reduced and/or avoided in this way by the use of dynamic shimming. Variations in the magnetic resonance image data between different sections, in particular different slices, which are often increased by dynamic shimming compared to global shimming, are reduced. In particular, the unnatural course of the depicted anatomy of the examination object between different sections potentially caused by the different shim parameter sets within the sections of the examination region is reduced or prevented thereby.

In an embodiment, a second B0 field map can be calculated using the first B0 field map and the plurality of shim parameter sets and the magnetic resonance image data is reconstructed from the magnetic resonance scan data using the first B0 field map and the plurality of shim parameter sets by using the second B0 field map. The multiple shim parameter sets and the first B0 field map are therefore used, in particular, by way of an indirect route, namely by the second B0 field map calculated using the first B0 field map and the plurality of shim parameter sets, in the reconstruction of the magnetic resonance image data. The second B0 field map can be calculated using the first B0 field map and the plurality of shim parameter sets, for example as described below, but also by a different approach that is considered appropriate to those skilled in the art. The first B0 field map and the multiple shim parameter sets can be used in the reconstruction of the magnetic resonance image data by the calculation of the second B0 field map. It should be noted in this connection that this approach advantageously does not require any additional acquisition time. The B0 inhomogeneities that remain after shimming are not scanned again for reconstruction of the magnetic resonance image data. Instead they are calculated from the first B0 field map, which is required anyway for shimming or for a field mapping technique.

In another embodiment, the second B0 field map is calculated using the first B0 field map and the multiple shim parameter sets such that a first spatial section of the second B0 field map is calculated using a first spatial section of the first B0 field map and of the first shim parameter set, and a second section of the second B0 field map is calculated using a second spatial section of the first B0 field map and of the second shim parameter set. The first spatial section can correspond in terms of its dimensions and/or position to the first section of the examination region. The second spatial section can correspond in terms of its dimensions and/or position to the second section of the examination region. The section-by-section calculation of the second B0 field map can ensure that the multiple shim parameter sets with the respectively appropriate spatial region information is taken into account in the calculation of the second B0 field map.

In another embodiment, in the reconstruction of magnetic resonance image data from the magnetic resonance scan data comprises, a first image region of the magnetic resonance image data is reconstructed using the first spatial section of the second B0 field map, and a second image region of the magnetic resonance image data is reconstructed using the second spatial section of the second B0 field map. The magnetic resonance image data is accordingly reconstructed, in particular for the various sections of the examination region, using different spatial sections of the second B0 field map. It can therefore be ensured that a spatially specific item of homogeneity information of the main magnetic field is suitably incorporated in the reconstruction of the magnetic resonance image data.

In another embodiment, the second B0 field map is calculated using the first B0 field map and the plurality of shim parameter sets such that B0 field contributions, resulting from the plurality of shim parameter sets, are offset against the first B0 field map. The B0 field contributions are advantageously offset separately against the first B0 field map for different shim parameter sets of the plurality of shim parameter sets. Following the mathematical removal of the B0 field contributions of the plurality of shim parameter sets from the first B0 field map, the second B0 field map can be incorporated in the reconstruction of the magnetic resonance image data.

In another embodiment, the magnetic resonance scan data of the examination region of the examination object are acquired by means of an echo planar imaging method. Echo planar imaging (EPI) typically allows images with moderate resolution to be acquired in intervals in the order of 100 ms. As a rule, the short acquisition period is used clinically for the acquisition of time series with high time resolution, for example in functional magnetic resonance tomography. A high level of insensitivity to movements also results from the short acquisition time. Echo planar imaging is therefore often used in diffusion-weighted imaging. In the case of magnetic resonance scan data recorded by echo planar imaging, local B0 inhomogeneities typically lead to geometric distortions and/or signal loss. The inventive approach, which can compensate both the geometric distortions and the signal loss, can accordingly be used in echo planar imaging. Furthermore, diffusion-weighted images should often be merged with morphological MR images which are not recorded by echo planar imaging or using other imaging modalities, so, for example, simplified evaluation of the images is possible. Largely complete distortion correction of the magnetic resonance image data recorded by echo planar imaging is particularly advantageous for this.

In another embodiment, the second B0 field map is converted into a pixel shift map, and the magnetic resonance image data are reconstructed from the magnetic resonance scan data using this pixel shift map. This approach is also called a field mapping technique. This is a combined acquisition and post-processing technique. The field mapping technique is described, for example, in the document Jezzard and Balaban, "Correction for Geometric Distortion in Echo Planar Images from $B_0$ Field Variations", 1995, MRM, 34, 65-73. The pixel shift map can describe a deformation field by means of which distortions can be reversed in the reconstruction of the magnetic resonance image data. The field mapping technique can correct distortions in the reconstruction of the magnetic resonance image data pixel-by-pixel. Distortion correction with the use of the pixel shift map, which is calculated on the basis of the second B0 field map, can allow remaining pixel shifts to be compensated pixel-by-pixel. It is precisely the combination of the field mapping technique with dynamic shimming that is particularly advantageous since, as a rule, the field mapping technique can only correct distortions and cannot restore lost signals. Signal losses can be avoided, however, by the use of dynamic shimming.

In another embodiment, the reconstruction of the magnetic resonance image data from the magnetic resonance scan data comprises a first reconstruction step and a second reconstruction step, wherein provisional magnetic resonance image data is reconstructed from the magnetic resonance scan data in the first reconstruction step and the provisional magnetic resonance image data are distortion corrected by the pixel shift map in the second reconstruction step. The reconstruction of the magnetic resonance image data is established in a two-step method in this way. The provisional magnetic resonance image data is reconstructed without taking into account the B0 field map and/or the plurality of shim parameter sets. The B0 field map and the multiple shim parameter sets are only then incorporated in the second reconstruction step. In this way a straightforward and fast reconstruction of the magnetic resonance image data is possible. As a rule, the provisional magnetic resonance image data are not displayed for a user.

In another embodiment, the second B0 field map is directly incorporated in the reconstruction of the magnetic resonance image data from the magnetic resonance scan data. The second B0 field map can be directly taken into account in a transformation between the magnetic resonance scan data and the magnetic resonance image data. In this way the second B0 field map does not have to be converted first in order for it to be taken into account in the reconstruction of the magnetic resonance image data. The second B0 field map is advantageously incorporated in this way as input parameters in an algebraic method, by means of which the magnetic resonance scan data is transformed into the magnetic resonance image data.

In another embodiment, the B0 field is scanned using raw data which comprises at least three echo signals that are each acquired following an excitation of the examination region. A specific choice of the echo time difference between the first and last echo signals means the B0 field maps, which are calculated from phase differential images of the first and last echo signals, depend only on the local B0 deviation and not on the spectral composition of the tissue. The B0 field map calculated from the phase difference between the first and last echo signals can then be unwrapped, i.e. phase envelopes as a consequence of the $2\pi$ periodicity of the phase can be mathematically removed. The signals of the intermediate echoes can be used, inter alia, for an absolute calibration of the unwrapped B0 field map. As a result, a B0 field map can be calculated in which a pixel value is proportional to the local absolute deviation from the resonance frequency. This has the advantage that the RF center frequency (shim channel of the $0^{th}$ order) can also be directly determined from the B0 field map. A separate frequency adjustment within the respective sections can be omitted thereby.

The inventive magnetic resonance apparatus has a scanner with a shim unit having at least one shim channel, a field map scan unit, scan data acquisition unit, adjusting unit and a computer that has a division processor, an ascertaining processor and a reconstruction processor, wherein the magnetic resonance apparatus is designed to implement the inventive method.

The magnetic resonance apparatus is therefore designed to implement a method for magnetic resonance imaging an examination object in an examination region. The division processor is configured to divide the examination region into multiple sections. The scanner is operated to scan the B0 field in the examination region, whereby a first B0 field map is generated. The ascertaining processor is configured to ascertain a number of shim parameter sets for the at least one shim channel using the first B0 field map, wherein a first shim parameter set of the number of shim parameter sets is ascertained for a first section of the multiple sections, and a second shim parameter set of the number of shim parameter sets is ascertained for a second section of the multiple sections. The scan data acquisition scanner is operated to acquire magnetic resonance scan data of the examination region of the examination object, wherein, before acquisition of the magnetic resonance scan data from the first section, the at least one shim channel is adjusted using the first shim parameter set by the adjusting processor and, before acquisition of the magnetic resonance scan data from the second section, the at least one shim channel is adjusted using the second shim parameter set by the adjusting processor. The reconstruction processor is configured to reconstruct magnetic resonance image data from the magnetic resonance scan data using the first B0 field map and the number of shim parameter sets.

In an embodiment of the magnetic resonance apparatus, the magnetic resonance apparatus has a field map calculation processor, and the field map calculation processor and the reconstruction processor are configured to calculate a second B0 field map using the first B0 field map and the number of shim parameter sets, and the magnetic resonance image data are reconstructed from the magnetic resonance scan data using the first B0 field map and the number of shim parameter sets by using the second B0 field map.

In another embodiment of the magnetic resonance apparatus, the magnetic resonance apparatus has a field map calculation processor configured to calculate the second B0 field map using the first B0 field map and the number of shim parameter sets such that a first spatial section of the second B0 field map is calculated using a first spatial section of the first B0 field map and the first shim parameter set, and a second section of the second B0 field map is calculated using a second spatial section of the first B0 field map and the second shim parameter set.

In another embodiment of the magnetic resonance apparatus, the magnetic resonance apparatus has a field map calculation processor, and the field map calculation processor and the reconstruction processor are configured such that, in the reconstruction of magnetic resonance image data from the magnetic resonance scan data, a first image region of the magnetic resonance image data is reconstructed using the first spatial section of the second B0 field map, and a second image region of the magnetic resonance image data is reconstructed using the second spatial section of the second B0 field map.

In another embodiment of the magnetic resonance apparatus, the magnetic resonance apparatus has a field map calculation processor configured to calculate the second B0 field map using the first B0 field map and the number of shim parameter sets such that B0 field contributions, resulting from the number of shim parameter sets, are offset against the first B0 field map.

In another embodiment of the magnetic resonance apparatus, the scan data acquisition scanner is operated to acquire the magnetic resonance scan data of the examination region of the examination object by an echo planar imaging method.

In another embodiment of the magnetic resonance apparatus, the magnetic resonance apparatus has a field map calculation processor configured to convert the second B0 field map into a pixel shift map, and the magnetic resonance image data are reconstructed from the magnetic resonance scan data using the pixel shift map.

In another embodiment of the magnetic resonance apparatus, the magnetic resonance apparatus has a field map calculation processor, and the field map calculation processor and the reconstruction processor are configured such that the reconstruction of the magnetic resonance image data from the magnetic resonance scan data includes a first reconstruction step and a second reconstruction step, wherein provisional magnetic resonance image data are reconstructed from the magnetic resonance scan data in the first reconstruction step and the provisional magnetic resonance image data are distortion-corrected by the pixel shift map in the second reconstruction step.

In another embodiment of the magnetic resonance apparatus, the magnetic resonance apparatus has a field map calculation processor, and the field map calculation processor and the reconstruction processor are configured to incorporate the second B0 field map directly in the reconstruction of the magnetic resonance image data from the magnetic resonance scan data.

In another embodiment of the magnetic resonance apparatus the scanner is operated to scan the B0 field using raw data that include at least three echo signals that are each acquired following an excitation of nuclear spins in the examination region.

The invention also encompasses a non-transitory, computer-readable data storage medium that can be loaded directly into a memory of a programmable computer of a magnetic resonance apparatus, and that is encoded with program code to carry out the inventive method when the code is executed in the computer of the magnetic resonance apparatus. The inventive method can consequently be carried out quickly, robustly and in a manner that can be repeated in an identical manner. The computer must have, for example, an appropriate main memory, an appropriate graphics card or an appropriate logic unit, so the respective method steps can be carried out efficiently. The computer can be directly connected to the magnetic resonance scanner or can be designed as part of the magnetic resonance apparatus. Examples of electronically readable data carriers are a DVD, magnetic tape or a USB stick, on which electronically readable control information, in particular software (cf. above), is stored.

The advantages of the inventive magnetic resonance apparatus and of the inventive storage medium essentially correspond to the advantages of the inventive method, which have been described above in detail. Features, advantages or alternative embodiments mentioned in this connection are similarly applicable to the other aspects of the invention. The functional features of the method are formed by appropriate physical modules, in particular hardware modules.

DESCRIPTION OF THE PREFERRED EMBODIMENTS

Figure 1:
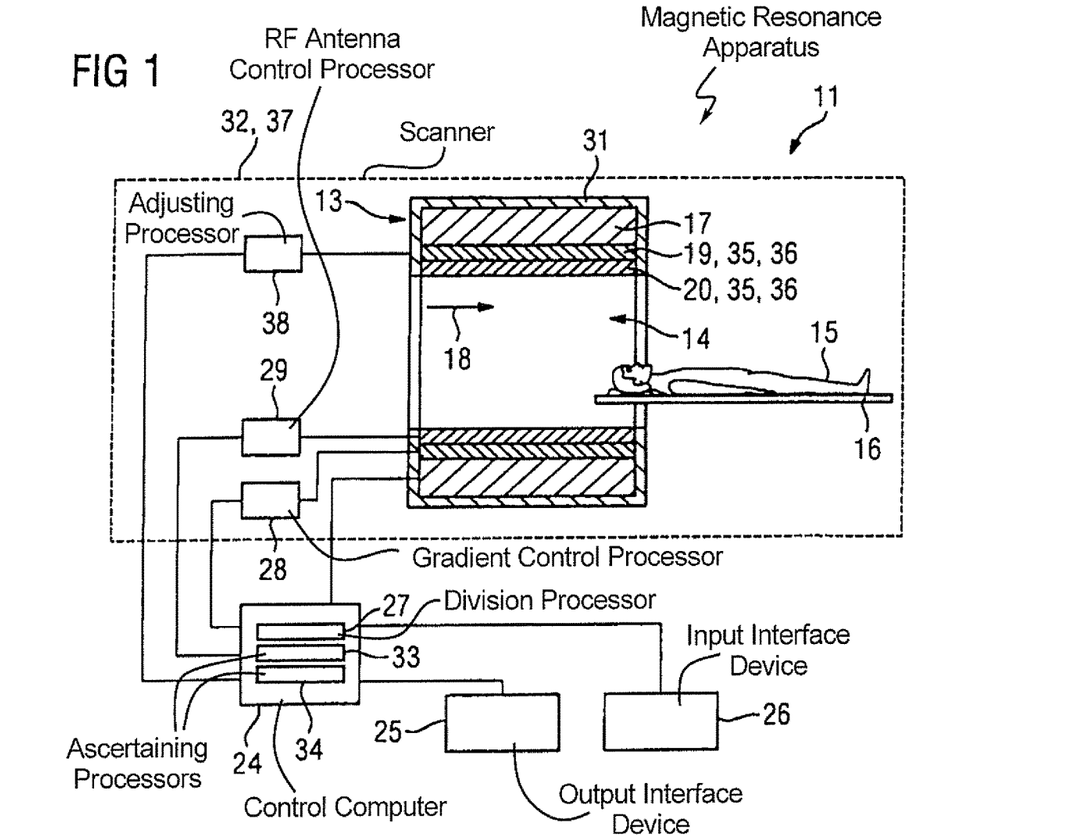
FIG. 1 schematically illustrates an inventive magnetic resonance apparatus in accordance with the invention.

FIG. 1 schematically shows an inventive magnetic resonance apparatus 11. The magnetic resonance apparatus 11 has a data acquisition scanner that includes a magnet unit 13, having a basic field magnet 17 that generates a strong, constant basic magnetic field 18. The scanner 32 has a cylindrical patient-receiving region 14 for receiving an examination object 15, in the present case a patient, with the patient-receiving region 14 being cylindrically surrounded in a circumferential direction by the magnet unit 13. The patient 15 can be moved by a patient-positioning device 16 of the magnetic resonance apparatus 11 into the patient-receiving region 14. The patient-positioning device 16 has for this purpose an examination table arranged so as to move inside the scanner 32. The magnet unit 13 is shielded from the outside by a housing shell 31.

The scanner 32 also has a gradient coil arrangement 19 that generates magnetic field gradients that are used for spatial encoding during imaging. The gradient coil arrangement 19 is controlled by a gradient control processor 28. The scanner 32 also has a radio-frequency antenna 20, which is designed in the illustrated case as a body coil permanently integrated in the scanner 32, and a radio-frequency antenna control processor 29 that operates the antenna 20 so as to excite nuclear spins in the object 15 so as to cause the excited nuclear spins to deviate from the polarization that is established in the basic magnetic field 18 generated by the basic field magnet 17. The radio-frequency antenna unit 20 is controlled by the radio-frequency antenna control processor 29 and to radiate radio-frequency magnetic resonance sequences into an examination space that is essentially formed by the patient-receiving region 14. The radio-frequency antenna unit 20 is also designed to receive magnetic resonance signals, in particular from the patient 15 that occur as the excited nuclear spins relax.

For controlling the basic field magnet 17, the gradient control processor 28 and the radio-frequency antenna control processor 29, the magnetic resonance apparatus 11 has a control computer 24. The control computer 24 centrally controls the magnetic resonance apparatus 11, such as, to carry out a predetermined imaging gradient echo sequence. Control information, such as imaging parameters, and reconstructed magnetic resonance images, can be supplied for a user at an output interface device 25, in the present case a display monitor, of the magnetic resonance apparatus 11. Furthermore, the magnetic resonance apparatus 11 has an input interface device 26, via which a user can enter information and/or parameters during a scanning process. The control computer 24 can include the gradient control processor 28 and/or radio-frequency antenna control processor 29 and/or the output interface device 25 and/or the input interface device 26. In the illustrated case the control computer 24 has a division processor 27, a first ascertaining processor 33 and a second ascertaining processor 34. These processors can be separate from each other or combined.

The magnetic resonance apparatus also has a shim unit 35, having at least one shim channel 36. To adjust the shim unit 35, the magnetic resonance apparatus has an adjusting processor 38, which is connected to the computer 24 with respect to data exchange.

The shim unit 35 has, for example, three shim channels 36. In the case illustrated in FIG. 1 the three shim channels 36 are formed by the three gradient coils of the gradient coil unit 19. These three shim channels 36 can generate shim fields in the x-direction, y-direction and in the z-direction. For example, the x-direction runs along a horizontal body axis of an examination object 15 lying on their back, the y-direction along the vertical body axis of the examination object 15, and the z-direction along a sagittal axis of the examination object 15. For different reasons, the gradient coils and gradient amplifiers are designed such that the gradient fields can be varied on a timescale of a few microseconds. In other words, this time is short compared to the time that passes between acquisition of data from different sections and/or slices of an examination region. The three shim channels 37 of the first order can typically be used for dynamic shimming therefore. The shim unit 35 can also have dedicated shim channels 36, in particular dedicated shim coils.

Furthermore, the shim unit 35 has an RF center frequency. For a specific shim parameter set the RF center frequency indicates the mean deviation of the resonance frequency within the section, to which the respective shim parameter set is allocated, from the RF center frequency that was adjusted during acquisition of the first B0 field map. The RF center frequency can be formally treated like a shim channel, namely a shim channel of the $0^{th}$ order.

The scan data acquisition scanner 32 is formed by the magnet unit 13 together with the radio-frequency antenna control processor 29 and the gradient control processor 28. The scan data acquisition scanner 32 can include the field map acquisition processor 37.

The magnetic resonance device 11 is therefore designed, together with the scan data acquisition scanner 32, adjusting processor 35, field map scanner 37, computer 24 and shim unit 35 for carry out the inventive method for magnetic resonance imaging.

The illustrated magnetic resonance apparatus 11 can have further components that magnetic resonance apparatuses conventionally have. The general operation of a magnetic resonance apparatus is known to those skilled in the art, moreover, so a detailed description of the further components is not necessary herein.

Figure 2:
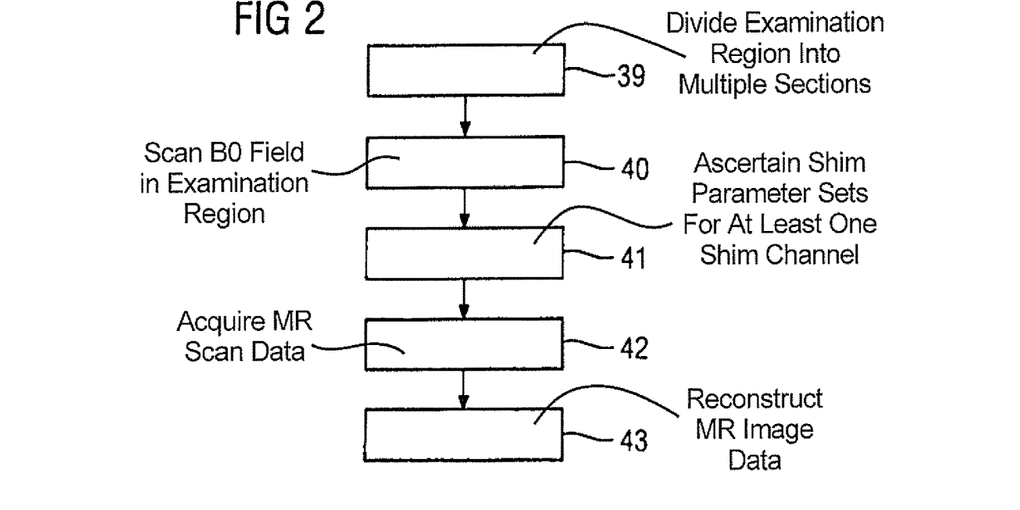
FIG. 2 is a flowchart of a first embodiment of the inventive method.

FIG. 2 is a flowchart of a first embodiment of an inventive method for magnetic resonance imaging in an examination region of an examination object 15 by operation of the magnetic resonance apparatus 11.

In a first method step 39 the examination region is divided into multiple sections by means of the division processor 27.

For example, each excitation slice of a slice stack forms a section of the plurality of sections.

In a further method step 40 the B0 field in the examination region is scanned by the field map scanner 37, wherein a first B0 field map is generated.

In a further method step 41 a number of shim parameter sets is ascertained for the at least one shim channel 36 using the first B0 field map by the ascertaining processor 33, wherein a first shim parameter set of the number of shim parameter sets is ascertained for a first section of the multiple sections, and a second shim parameter set of the plurality of shim parameter sets is ascertained for a second section of the multiple sections.

In a further method step 42, magnetic resonance scan data of the examination region of the examination object 15 are acquired by operation of the scan data acquisition scanner 32, but before acquisition of the magnetic resonance scan data from the first section, the at least one shim channel 36 is adjusted using the first shim parameter set by the adjusting unit 38 and, before acquisition of the magnetic resonance scan data from the second section, the at least one shim channel 36 is adjusted using the second shim parameter set by the adjusting unit 38.

In a further method step 43 magnetic resonance image data are reconstructed from the magnetic resonance scan data using the first B0 field map and the number of shim parameter sets by means of the reconstruction processor 34.

Figure 3:
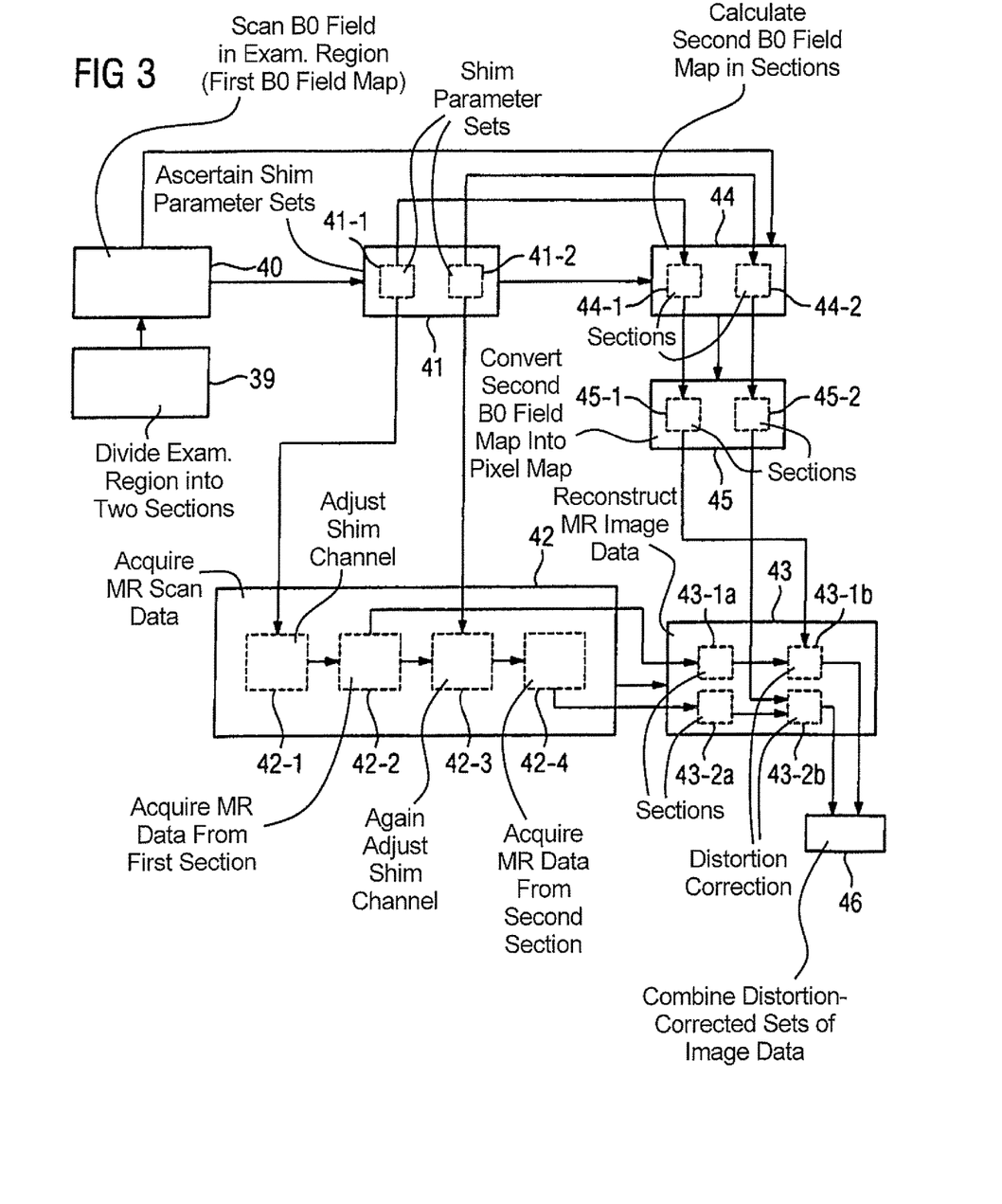
FIG. 3 is a flowchart of a second embodiment of the inventive method.

FIG. 3 is a flowchart of a second embodiment of an inventive method for magnetic resonance imaging in an examination region of an examination object 15 by operation of the magnetic resonance apparatus 11.

The following description is essentially limited to the differences from the exemplary embodiment in FIG. 2, with reference being made in respect of unchanging method steps to the description of the exemplary embodiment in FIG. 2. Method steps that essentially stay the same are basically numbered with the same reference numerals.

The embodiment of the inventive method shown in FIG. 3 essentially comprises method steps 40, 41, 42, 43 of the first embodiment of the inventive method according to FIG. 2. The embodiment of the inventive method shown in FIG. 3 has additional method steps and substeps. An alternative method sequence to FIG. 3 is also conceivable which has just some of the additional method steps and/or substeps shown in FIG. 2. Of course, an alternative method sequence to FIG. 3 can also have additional method steps and/or substeps.

In the example of FIG. 3 it is assumed for a better overview that the examination region is divided into two sections in the first method step 39, i.e., for example, has two individual slices. The concept may of course be arbitrarily expanded to a division into more sections.

In a further method step 40, a first B0 field map is acquired before ascertaining the plurality of shim parameter sets. The first B0 field map can be scanned using raw data which comprises at least three echo signals which are each acquired following an excitation of the examination region. The first B0 field map represents local deviations from an ideal constant basic magnetic field 18 within the plurality of sections of the examination region. The first B0 field map can also be converted into a first frequency map which reproduces a local deviation of a local resonance frequency from a system frequency. A frequency map $\Delta f(x,y,z)$ and a B0 field map $\Delta B_0(x,y,z)$ may typically be converted such that:

$$\Delta f(x,y,z) = (\gamma/(2\pi)) \times \Delta B_0(x,y,z)$$

Here $\gamma/(2\pi)$ is the gyromagnetic ratio which for protons is 42.576 MHz/T.

Of course, a frequency map can also be ascertained first of all which can then be converted into a B0 map. The same applies to phase maps which primarily reproduce a phase change between the individual echo signals.

The number of first shim parameter sets is ascertained in a further method step 41 using the first B0 field map. Here a first shim parameter set is ascertained in a first substep 41-1 of the further method step 41 using the first B0 field map, and a second shim parameter set is ascertained in a second substep 41-2 of the further method step 41 a using the first B0 field map. Of course even further section shim data sets can also be ascertained. In particular, a shim parameter set can be ascertained for each slice of the examination region.

The first shim parameter set $\Delta f_0^{(1)}$, $\Delta G_x^{(1)}$, $\Delta G_y^{(1)}$, $\Delta G_z^{(1)}$ comprises, in particular, a first RF center frequency $\Delta f_0^{(1)}$, a first x-gradient offset current $\Delta G_x^{(1)}$ for the gradient coil in the x-direction, a first y-gradient offset current $\Delta G_y^{(1)}$ for the gradient coil in the y-direction and a first z-gradient offset current $\Delta G_z^{(1)}$ for the gradient coil in the z-direction. The first shim parameter set $\Delta f_0^{(1)}$, $\Delta G_x^{(1)}$, $\Delta G_y^{(1)}$, $\Delta G_z^{(1)}$ is advantageously chosen such that local field deviations $\Delta B_0(x,y,z)$ in the first section are optimally compensated.

The second shim parameter set $\Delta f_0^{(2)}$, $\Delta G_x^{(2)}$, $\Delta G_y^{(2)}$, $\Delta G_z^{(2)}$ comprises, in particular, a second RF center frequency $\Delta f_0^{(2)}$, a second x-gradient offset current $\Delta Gx_x^{(2)}$ for the gradient coil in the x-direction, a second y-gradient offset current $\Delta G_y^{(2)}$ for the gradient coil in the y-direction and a second z-gradient offset current $\Delta G_z^{(2)}$ for the gradient coil in the z-direction. The second shim parameter set $\Delta f_0^{(2)}$, $\Delta G_x^{(2)}$, $\Delta G_y^{(2)}$, $\Delta G_z^{(2)}$ is advantageously chosen such that local field deviations $\Delta B_0(x,y,z)$ in the second section are optimally compensated.

To ascertain the first shim parameter set and/or the second shim parameter set an equation with the following form can be deployed for each pixel of the first B0 field map within the first section and/or the second section:

$$-\Delta B_o(x, y, z) = \frac{2\pi}{\gamma}\Delta f_0 + \Delta G_x(x - x_0) + \Delta G_y(y - y_0) + \Delta G_z(z - z_0)$$

Herein $(x_0, y_0, z_0)$ is the coordinate of an isocenter of the gradient coil unit 19 within the first B0 field map. The isocenter is the location at which the field contribution of the gradient coil unit 19 is zero. $\Delta G_x$ indicates a change in the gradient field in the x direction of the first B0 field map with respect to the adjustment during acquisition of the first B0 field map. Accordingly, $\Delta G_y$ and $\Delta G_z$ indicate a change in the gradient field in the y and z directions respectively of the first B0 field map with respect to the corresponding adjustment during acquisition of the first B0 field map. $\Delta f_0$ indicates a change in an RF center frequency with respect to the adjustment during acquisition of the first B0 field map.

As a whole, these equations form an overdetermined linear equation system for each section of the examination region, and this can be solved using standard methods. The four unknown $\Delta f_0^{(1)}$, $\Delta G_x^{(1)}$, $\Delta G_y^{(1)}$, $\Delta G_z^{(1)}$ of the first shim parameter set or $\Delta f_0^{(2)}$, $\Delta G_x^{(2)}$, $\Delta G_y^{(2)}$, $\Delta G_z^{(2)}$ of the second shim parameter set can therefore each be ascertained. If creation of the first B0 field map is based on the scan of the phase difference between acquired MR images with a different echo time then no information about the local B0 field deviation can be obtained from pixels that essentially contain only noise. Pixels of this kind should therefore be excluded from the solution to the equation systems. This can occur by background segmenting and/or weighting of the individual equations proportionally to the pixel value of a magnitude image at the location (x,y,z). The magnitude image can likewise be extracted from the magnetic resonance scan data that is acquired in order to create the first B0 field map.

In a further method step 44, a second B0 field map is calculated using the first B0 field map and using the plurality of shim parameter sets. The second B0 field map is calculated using the first B0 field map and using the plurality of shim parameter sets such that B0 field contributions, resulting from the number of shim parameter sets, are offset against the first B0 field map. Here, in particular a spatial section of the first B0 field map is offset against the B0 field contributions resulting from an appropriate suitable first shim parameter set of the number of first shim parameter sets, with the appropriate first shim parameter set having been specifically ascertained for the section of the multiple sections that corresponds to the spatial section.

In the illustrated case a first section of the second B0 field map is calculated in a first substep 44-1 of the further method step 44 using the first spatial section of the first B0 field map and the first shim parameter set ascertained for the first section. In a second substep 44-2 of the further method step 44 a second spatial section of the second B0 field map is calculated using the second spatial section of the first B0 field map and the second shim parameter set ascertained for the second section. The second B0 field map thereby comprises the first spatial section and the second spatial section.

To calculate the second B0 field map the B0 field contributions of the shim parameter set ascertained for the respective section for the at least one first shim channel 36 are added to the first B0 field map pixel-by-pixel, for example for each section. This means that the second B0 field map represents a new virtual B0 field map $\Delta B_0'(x,y,z)$, to which the following applies:

$$\Delta B_0'(x, y, z) = \Delta B_o(x, y, z) + \begin{cases} \frac{2\pi}{\gamma}\Delta f_0^{(1)} + \Delta G_x^{(1)}(x-x_0) + \Delta G_y^{(1)}(y-y_0) + \Delta G_z^{(1)}(z-z_0), \text{ if } (x, y, z) \in V1 \\ \frac{2\pi}{\gamma}\Delta f_0^{(2)} + \Delta G_x^{(2)}(x-x_0) + \Delta G_y^{(2)}(y-y_0) + \Delta G_z^{(2)}(z-z_0), \text{ if } (x, y, z) \in V2 \end{cases}$$

wherein V1 denotes the first section, V2 the second section and the element sign from the set theory here represents "the pixel considered having coordinates (x,y,z) belongs to the first section V1 or to the second section V2". The second, in particular virtual, B0 field map $\Delta B_0'(x,y,z)$ will, generally, have lower B0 field deviations than the original scanned first B0 field map $\Delta B_0(x,y,z)$. Locally within a section the second B0 field map can approximately reproduce the B0 field characteristic following adjustment of the at least one shim channel 36 using the respective shim parameter sets.

In a further method step 45, the second B0 field map can be converted into a pixel shift map. The pixel shift map comprises a first spatial section and a second spatial section. The first spatial section of the pixel shift map is calculated in a first substep 45-1 of the further method step 45 using the first spatial section of the second B0 field map. The second spatial section of the pixel shift map is calculated in a second substep 45-2 of the further method step 45 using the second spatial section of the second B0 field map.

One basis for calculation of the pixel shift map is that a local field deviation $\Delta B_0'(x,y,z)$, particularly in echo planar imaging, causes the following local shift of the object in the phase coding direction $\Delta d_{pe}$:

$$\Delta d_{pe}(x, y, z) = (\gamma/(2\pi))\Delta B_0'(x, y, z)ES_{pe}FoV_{pe} = \Delta f'(x, y, z)ES_{pe}FoV_{pe}^{phys}$$

wherein $ES_{pe}$ is the echo spacing in the phase coding direction, i.e. the time between the acquisition of two successive phase coding rows, and $FoV_{pe}^{phys}$ is the size of the physical field of view in the phase coding direction. The superscript index "phys" stands for 'physical' and should serve a reminder that the physical field of view should be taken which, in the case of oversampling in the phase coding direction, is increased by a factor $(1+OS_{pe})$ with respect to the $FOV_{pe}$ adjusted by the user in the phase coding direction. The factor $OS_{pe}$ indicates by which factor the row spacing is shortened in the k-space with respect to the row spacing calculated according to the Nyquist criterion for the adjusted $FOV_{pe}$. The echo interval parameters $ES_{pe}$ and $FOV_{pe}$ are known as scanning parameters. The size of a pixel in the phase coding direction is $$\Delta y_{PE} = FoV_{pe}/NIma_{pe} = FoV_{pe}^{phys}/FTLen_{pe}$$

wherein $NIma_{pe}$ is the number of image rows in the phase coding direction and $FTLen_{pe}$ the Fourier transformation length in the phase coding direction. From this the shift $\Delta d'$ in units of pixels is $$\Delta d'_{pe}(x,y,z) = (\gamma/(2\pi))\Delta B_0'(x,y,z)ES_{pe}/FTLen_{pe}$$

$$\rightarrow \Delta d'_{pe}(x,y,z) = \Delta f'(x,y,z)ES_{pe}FTLen_p$$

This preceding formula is the sought conversion of the second B0 field map $\Delta B_0'(x,y,z)$, or a second field map $\Delta f'(x,y,z) = (\gamma/(2\pi))\Delta B_0'(x,y,z)$ calculated from the second B0 field map, into a pixel shift map.

Therefore, apixel, which is localized at position $(x, y^{undistor}, z)$ in an undistorted image, is shifted to the location $(x, y^{undistor} + \Delta d'_{pe}(x, y^{undistor}, z), z)$ in the distorted image. Without limiting the generality it is assumed that the phase coding direction coincides with the y direction.

In a first approximation an undistorted image is therefore obtained by replacing the intensity value at position $(x, y^{undistor}, z)$ with the scanned value at position $(x, y^{undistor} + \Delta d'_{pe}(x, y^{undistor}, z), z)$:

$$I^{undist}(x, y^{undistor}, z) = I^{dist}(x, y^{undistor} + \Delta d'_{pe}(x, y^{undistor}, z), z)$$

Since $\Delta d'_{pe}(x, y^{undistor}, z)$ is generally not an integer an interpolation is typically required with this operation. Furthermore, the intensity value of the pixel can be corrected with the aid of the gradient of the shift map $\Delta d'_{pe}(x,y,z)$ in the phase coding direction.

As an alternative to the approach shown in FIG. 3 the further method step 45 can be omitted; conversion of the second B0 field map is not imperative. This kind of approach is described below.

The magnetic resonance image data are typically acquired in further method step 42 in a nested 2D multi-slice scan. The number of slices can typically be between 5 and 50. Each of these slices can have a thickness of typically 2 mm to 10 mm. The field of view of a slice is typically between 200×200 mm² (for example in the case of an axial head examination) and 400×400 mm² (for example in the case of an abdominal examination). As a rule, the slices are oriented parallel to each other with a gap of 0 to 50 percent of the slice thickness between adjacent slices. Each of these slices and/or a section of each slice can represent a section of the examination region. In the illustrated case there are only two sections of the examination region for the sake of clarity, however. The time between acquisition of data of different slices is TR/N, where TR is the repetition time and N the number of slices from which data is acquired in a repetition interval. This time is typically in the order of 5 ms to a few 100 ms. The parameters described here are only examples of course. In further method step 42 the magnetic resonance image data can also be acquired using scanning parameters other than the ones described. The magnetic resonance scan data of the examination region of the examination object 15 is acquired here, in particular, by means of an echo planar imaging method.

In a first substep 42-1 of the further method step 42 the at least one shim channel 36 is adjusted using the first shim parameter set of the plurality of shim parameter sets. The gradient offset currents $\Delta G_x^{(1)}$, $\Delta G_y^{(1)}$, $\Delta G_z^{(1)}$ are added to the gradient offset currents that were adjusted during acquisition of the first B0 field map. The adjustment of the center frequency can be changed with respect to the adjustment during acquisition of the first B0 field map by $\Delta f_0^{(1)}$.

In a second substep 42-2 of the further method step 42 magnetic resonance scan data is then acquired from the first section. The at least one shim channel 36 remains adjusted for acquisition of the magnetic resonance scan data from the first section using the first shim parameter set.

In a third substep 42-3 of the further method step 42 the at least one shim channel 36 is then adjusted using the second shim parameter set of the plurality of shim parameter sets. The gradient offset currents $\Delta G_x^{(2)}$, $\Delta G_y^{(2)}$, $\Delta G_z^{(2)}$ are added to the gradient offset currents that were adjusted during acquisition of the first B0 field map. The adjustment of the center frequency can be changed with respect to the adjustment during acquisition of the first B0 field map by $\Delta f_0^{(2)}$.

It should be noted in this connection that when adjusting the at least one shim channel 36 for a specific section, there need only be activity between transmission and receiving paths of the magnetic resonance sequence. Whether, for example, the gradient offset currents are switched on before a first high-frequency excitation pulse within a section or, for example, only with a slice selection gradient of the first high-frequency excitation pulse is typically irrelevant in a first approximation therefore. Owing to unavoidable eddy currents as a consequence of the gradient switching operation, it can nevertheless be expedient to adjust the at least one shim channel 36 using the shim parameter sets slightly earlier than is absolutely necessary.

In a fourth substep 42-4 of the further method step 42, magnetic resonance scan data are then acquired from the second section. The at least one shim channel 36 remains adjusted for acquisition of the magnetic resonance scan data from the second section using the second shim parameter set.

Reconstruction of the magnetic resonance image data from the magnetic resonance scan data in a further method step 43 comprises a first reconstruction step 43-1a, 43-2a and a second reconstruction step 43-1b, 43-2b, wherein provisional magnetic resonance image data is reconstructed from the magnetic resonance scan data in the first reconstruction step 43-1a, 43-2a. In a first substep 43-1a of the first reconstruction step 43-1a, 43-2a provisional magnetic resonance image data is reconstructed from the magnetic resonance scan data acquired from the first section in the second substep 42-2 of further method step 42. In a second substep 43-2a of the first reconstruction step 43-1a, 43-2a provisional magnetic resonance image data are reconstructed from the magnetic resonance scan data acquired from the second section in the fourth substep 42-4 of the further method step 42.

In a second reconstruction step 43-1b, 43-2b the provisional magnetic resonance image data are distortion-corrected by use of the pixel shift map. In this way the magnetic resonance image data is reconstructed from the magnetic resonance scan data using the pixel shift map.

In a first substep 43-1b of the second reconstruction step 43-1b, 43-2b a first image region of the magnetic resonance image data is reconstructed from the provisional magnetic resonance image data using the first region of the pixel shift map calculated in a first substep 45-1 of the further method step 45. The first image region of the magnetic resonance image data then forms distortion-corrected magnetic resonance image data which maps the first section of the examination region.

In a second substep 43-2b of the second reconstruction step 43-1b, 43-2b a second image region of the magnetic resonance image data is reconstructed from the provisional magnetic resonance image data using the second region of the pixel shift map calculated in the second substep 45-2 of the further method step 45. The second image region of the magnetic resonance image data then forms distortion-corrected magnetic resonance image data which maps the second section of the examination region.

Alternatively, the second B0 field map can also be incorporated in the reconstruction of the magnetic resonance image data in some other way. For example, the magnetic resonance image data can also be reconstructed directly from the magnetic resonance scan data by means of the second B0 field map, without the indirect route via the provisional magnetic resonance image data. Substeps 43-1a, 43-2a, in particular, of further method step 42 are then omitted. In this way the second B0 field map can be directly taken into account in the transformation between the acquired raw data S(k,l) of the magnetic resonance scan data and images I(m,n) of the magnetic resonance image data calculated therefrom:

$$S(k, l) = \sum_{m=0}^{M-1} \sum_{n=0}^{N-1} I(m, n) e^{-2\pi i \left[\frac{km}{M} + \frac{ln}{N} + \left(\frac{\gamma}{2\pi}\right) \Delta B'_0(m,n) t(k,l)\right]} \quad (1)$$

Therein S(k,l) is the scanned raw data point with the k-space coordinates k and l. I(m,n) denotes a pixel of the sought distortion-free image having the image space coordinates (m, n), where m is the row index, n the column index. M is the number of image rows and N the number of image columns. $\Delta B_0'(m,n)$ is the value of the pixel of the second B0 field map having these image space coordinates (m,n). t(k,l) is the time that elapses between acquisition of the raw data point having the k-space coordinates (k,l) and the respective RF excitation.

If the second field map $\Delta B_0'(m,n)$ is equal to zero then the equation corresponds to a discrete 2-dimensional Fourier transformation and k-space data can be effectively converted into image data using the fast Fourier transformation algorithm. If the second field map $\Delta B_0'(m,n)$ is not equal to zero the Fourier transformation leads to distorted images. In this case the equation (1) is a linear equation system:

$$S(k,l) = \sum_{m=0}^{M-1} \sum_{n=0}^{N-1} I(m,n) \quad (2)$$

mit $$A(k,l,m,n) = e^{-2\pi i \left[\frac{km}{M} + \frac{ln}{N} + \left(\frac{\gamma}{2\pi}\right)\Delta B_0'(m,n)t(k,l)\right]}$$

This can be solved using algebraic methods to calculate the distortion-free image I(m,n) from the acquired raw data S(k,l). In the case of large remaining B0 inhomogeneities the solution to the equation system falls into the category of what are known as ill-posed problems, so robust methods such as singular value decomposition or the conjugate gradient method are used to solve equation 2.

Since both the M×N image pixel matrix I(m,n) and the M×N raw data matrix S(k,l) can be written as a column vector with a length M·N and accordingly A can be written as an M·N×M·N matrix, the dimension of the equation system is generally very large. In the case of EPI row and column numbers are in the order of M=N=128, the equation system is therefore in the order of 16384×16384. By exploiting the fact that the time for acquisition of a single row is very short in the case of EPI, the time t(k,l) can be approximately set as a function of the row index.

$$t(k,l) \approx t(k) \quad (3)$$

This allows the large M·N×M·N equation system to be decomposed into N equation systems with a size M×M, i.e. one equation system each with a size M×M per image column. This reduces the numerical effort significantly. Furthermore, it is possible to convert the transformation (1), (2) between undistorted image I and raw data S into a transformation between undistorted image I and distorted image I', which can be calculated with the aid of a fast 2-dimensional Fourier transformation. This has the advantage that the associated matrix is sparsely filled. This in turn means that only a few matrix elements are not equal to zero. Sparsely filled systems can be particularly effectively solved using the conjugate gradient method.

In a further method step 46 the distortion-corrected magnetic resonance image data, which maps the first section, and the distortion-corrected magnetic resonance image data, which maps the second section, are combined to form an overall magnetic resonance image data record. This overall magnetic resonance image data record can then be output, for example, on the display unit 25 and/or stored in a database.

The method steps of the inventive method shown in FIG. 2-3 are performed by the computer 24. For this purpose the computer 24 has the requisite software and/or computer programs that are stored in a memory of the computer 24. The software and/or computer programs for program code configured to carry out the inventive method when the computer program and/or the software is run in the computer 24 by a processor thereof.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for magnetic resonance (MR) imaging of an examination region of an examination object by operation of an MR scanner comprising a shim unit having at least one shim channel, said method comprising:
   in a computer, dividing the examination region into multiple sections;
   operating the MR scanner to scan a basic magnetic field of the examination region produced by the MR scanner, and generating a B0 field map in said computer from the scanned basic magnetic field;
   in said computer, determining a plurality of shim parameter sets for said shim channel using said B0 field map, with a first shim parameter set among said plurality of shim parameter sets being determined for a first section of said multiple sections, and a second shim parameter set among said plurality of shim parameter sets being determined for a second section of said multiple sections;
   operating the MR scanner to acquire MR scan data from the examination region but, before acquiring the MR scan data from the first section, adjusting said shim channel using said first shim parameter set and, before acquiring said MR scan data from the second section, adjusting said shim channel using said second shim parameter set; and
   in said computer, reconstructing MR image data from the MR scan data using said B0 field map and said plurality of shim parameter sets, and making the reconstructed MR image data available from the computer in electronic form as a data file.

2. A method as claimed in claim 1 wherein said B0 field map is a first B0 field map, and comprising calculating a second B0 field map using said first B0 field map and said plurality of shim parameter sets, and reconstructing said MR image data from the MR scan data using said first B0 field map and said plurality of shim parameter sets and said second B0 field map.

3. A method as claimed in claim 2 comprising calculating said second B0 field map using said first B0 field map and said plurality of shim parameters by calculating a first spatial section of said second B0 field map using a first spatial section of said first B0 field map and said first shim parameter set and calculating a second spatial section of said second B0 field map using a second spatial section of said first B0 field map and said second shim parameter set.

4. A method as claimed in claim 3 comprising reconstructing said MR image data from said MR scan data by reconstructing a first image region of said MR image data using the first spatial section of the second B0 field map, and reconstructing a second image region of the MR image data using the second spatial section of the second B0 field map.

5. A method as claimed in claim 2 comprising calculating said second B0 field map using the first B0 field map and the plurality of shim parameter sets by offsetting B0 field contributions, which result from said plurality of shim parameter sets, against said first B0 field map.

6. A method as claimed in claim 5 comprising acquiring said MR scan data of the examination region by operating the MR scanner with an echo planar imaging method.

7. A method as claimed in claim 6 comprising, in said computer, converting said second B0 field map into a pixel shift map, and reconstructing said MR image data from said MR scan data using said pixel shift map.

8. A method as claimed in claim 7 comprising reconstructing said MR image data from said MR scan data in a first reconstruction step wherein provisional MR image data are reconstructed from the MR scan data, and in a second reconstruction step wherein said provisional MR image data are distortion-corrected using said pixel shift map.

9. A method as claimed in claim 6 comprising directly incorporating said second B0 field map into the reconstruction of the MR image data from the MR scan data.

10. A method as claimed in claim 1 comprising scanning said B0 field using raw data comprising at least three echo signals each acquired after an excitation of nuclear spins in the examination region.

11. A magnetic resonance (MR) for imaging of an examination region of an examination object, said MR apparatus comprising:
an MR scanner comprising a shim unit having at least one shim channel, and a basic field (B0 field) magnet that produces a basic magnetic field in the scanner;
a computer configured to divide the examination region into multiple sections;
said computer being configured to operate the MR scanner to scan the basic magnetic field in the examination region produced by the MR scanner, and to generate a B0 field map in said computer from the scanned basic magnetic field;
said computer being configured to determine a plurality of shim parameter sets for said shim channel using said B0 field map, with a first shim parameter set among said plurality of shim parameter sets being determined for a first section of said multiple sections, and a second shim parameter set among said plurality of shim parameter sets being determined for a second section of said multiple sections;
said computer being configured to operate the MR scanner to acquire MR scan data from the examination region but, before acquiring the MR scan data from the first section, to adjust said shim channel using said first shim parameter set and, before acquiring said MR scan data from the second section, to adjust said shim channel using said second shim parameter set; and said computer being configured to reconstruct MR image data from the MR scan data using said B0 field map and said plurality of shim parameter sets, and to make the reconstructed MR image data available from the computer in electronic form as a data file.

12. A non-transitory, computer-readable data storage medium encoded with programming instructions for magnetic resonance (MR) imaging of an examination region of an examination object by operation of an MR scanner comprising a shim unit having at least one shim channel, said MR scanner being operated by a computer and said storage medium being loaded into the computer and the programming instructions causing said computer to:

divide the examination region into multiple sections;

operate the MR scanner to scan a basic magnetic field of the examination region produced by the MR scanner, and generate a B0 field map in said computer from the scanned basic magnetic field;

determine a plurality of shim parameter sets for said shim channel using said B0 field map, with a first shim parameter set among said plurality of shim parameter sets being determined for a first section of said multiple sections, and a second shim parameter set among said plurality of shim parameter sets being determined for a second section of said multiple sections;

operate the MR scanner to acquire MR scan data from the examination region but, before acquiring the MR scan data from the first section, adjust said shim channel using said first shim parameter set and, before acquiring said MR scan data from the second section, adjust said shim channel using said second shim parameter set; and reconstruct MR image data from the MR scan data using said B0 field map and said plurality of shim parameter sets, and make the reconstructed MR image data available from the computer in electronic form as a data file.

* * * * *